US006022143A

United States Patent [19]
Helmreich

[11] Patent Number: 6,022,143
[45] Date of Patent: Feb. 8, 2000

[54] X-RAY SYSTEM WITH IMPROVED ACCESSIBILITY FOR THE USER

[75] Inventor: Gerhard Helmreich, Effeltrich, Germany

[73] Assignee: Siemens Aktiengesellschaft, Munich, Germany

[21] Appl. No.: 08/905,026

[22] Filed: Aug. 1, 1997

[30] Foreign Application Priority Data

Aug. 1, 1996 [DE] Germany .................... 196 31 136

[51] Int. Cl.[7] .................................................. H05G 1/02
[52] U.S. Cl. ........................................ 378/181; 378/195
[58] Field of Search .................................. 378/167, 177, 378/181, 195, 196, 197

[56] References Cited

U.S. PATENT DOCUMENTS

| | | | |
|---|---|---|---|
| 3,904,531 | 9/1975 | Barrett et al. | 378/181 |
| 3,967,126 | 6/1976 | Otto, Jr. | 378/177 |
| 3,986,034 | 10/1976 | Wittkopp et al. | 378/167 |
| 4,363,128 | 12/1982 | Grady et al. | 378/181 |
| 4,964,149 | 10/1990 | Little | 378/167 |
| 5,023,899 | 6/1991 | Ohlson | 378/198 |
| 5,349,628 | 9/1994 | Taniguruma et al. | 378/181 |
| 5,530,734 | 6/1996 | Jaeger | 378/181 |
| 5,636,259 | 6/1997 | Khutoryansky et al. | 378/197 |
| 5,703,925 | 12/1997 | Wright | 378/181 |
| 5,764,724 | 6/1998 | Ohlson | 378/177 |
| 5,870,450 | 2/1999 | Khutoryansky et al. | 378/181 |

Primary Examiner—David P. Porta
Assistant Examiner—Drew A. Dunn
Attorney, Agent, or Firm—Sughrue, Mion, Zinn, Macpeak & Seas, PLLC

[57] ABSTRACT

An X-ray system, in particular for radiological and angiographic methods, has a patient table arranged on a stand under a radiation source. The system further has a detector, which is mounted displaceably under a table plate. A carriage supporting the detector is mounted beneath the table plate such that it can be displaced in a sliding fashion in a longitudinal direction of the table by means of a positioning motor.

18 Claims, 6 Drawing Sheets

X-RAY SYSTEM WITH IMPROVED ACCESSIBILITY FOR THE USER

The following disclosure is based on German Patent Application No. 19631136.5, filed on Aug. 1, 1996.

FIELD OF AND BACKGROUND OF THE INVENTION

The invention relates to an X-ray system having a patient table arranged on a stand under a radiation source, and further having a detector, which is mounted displaceably under the table plate. Such systems can be fashioned in particular for radiological and angiographic procedures. The invention is associated with a variety of advantages, notably including the ability to omit the conventional C-arm from the X-ray system.

In conventional X-ray systems, the radiation source and the detector are arranged by means of horizontal support arms on a support column. This column is usually vertical but, if appropriate, can also be fashioned to be pivotable. This has the beneficial result that, irrespective of the displacement of the radiation source, the detector and the radiation source are always disposed exactly opposite one another, thus ensuring an optimum setting for producing the desired X-ray images. This arrangement has the disadvantage, however, that it necessitates an extremely large, complicated and expensive design. Additionally, there is no room for medical personnel on the side of the patient table where the movable column that supports the cross arms for the radiation source and the detector is located. As a result, e.g., when medical procedures are being carried out in the region of the X-ray system, it is not possible for the doctor or nurse to work on the side where the column is located.

OBJECTS AND SUMMARY OF THE INVENTION

It is therefore an object of the present invention to configure an X-ray system of the type described above with a simplified mechanical design and thereby ensure better accessibility from all directions to the patient lying on the table. It is a further object of the invention to provide an X-ray system in which the need for a bulky C-arm is avoided, yet the advantages associated with the conventional C-arm are nonetheless retained.

According to the invention, a carriage supporting the detector is mounted beneath the plate of the patient table such that it can be displaced in a sliding fashion in the longitudinal direction of the table by means of a positioning motor. The carriage is preferably guided on lateral longitudinal supports which are preferably permanently connected to the table plate.

Because the invention avoids the mechanical connection of the radiation source and detector via a C-shaped frame (C-arm), the support column, on which the two cross arms have so far needed to be arranged, can be completely omitted. The radiation source can be guided without difficulty on a rail above the table. The conventional cross arm for the carriage can also be eliminated, since the carriage beneath the table plate is guided, according to the invention, with the aid of a positioning motor longitudinally along the length of the table. A control device couples the movement of the carriage, and hence the detector, to that of the radiation source, to ensure the fixed relative positional relationship between the source and the detector. Consequently, the table plate, and thus also the patient lying thereon, can be accessed without difficulty at any time from all sides of the table. By way of contrast, in the conventional art, the only means known for achieving this fixed relationship is through mechanically coupling the source and detector through the support arms and the support column.

For reasons of cost, it is customary to fashion the detector less wide than the table. The present invention accommodates this customary design by providing the carriage with a transverse recess for displacing the detector transverse to the longitudinal direction of the table. This transverse displacement is preferably performed by a separate positioning motor which, just like the positioning motor for the longitudinal displacement of the carriage, is operable via a control device for coupling the movements of the radiation source and the detector.

Preferably, the positioning motors are driven, for the purpose of displacing the carriage, by means of a step control on the basis of the same control signals used for displacing the radiation source. In addition, it has proved to be particularly expedient in embodying the invention if the control device includes on the detector a sensor which can move the detector into the desired position beneath the radiation source. This sensor responds either to the X-ray signal itself or to an additional positioning signal output by the radiation source.

Finally, it is also within the scope of the invention that the longitudinal supports for the table plate and for the movable detector carriage are mounted beneath the detector carriage on at least one cross arm fastened to the table's stand. One advantage achieved thereby is that the cross arm(s) are movable within guides of the longitudinal supports between any one of a number of locked positions provided for the cross arm(s). Such an arrangement allows for longitudinal displacement of the table plate with the patient, and for a design modification in which it is possible for the table with the patient and the detector carriage to be tilted to any desired angle up to 90° from the horizontal.

BRIEF DESCRIPTION OF THE DRAWINGS

The invention and further advantages, features and details thereof are explained more particularly in the following description of an exemplary embodiment, with the aid of the diagrammatic drawings, in which.

DETAILED DESCRIPTION OF THE PREFERRED EMBODIMENTS

The X-ray system represented in FIGS. 1–4 includes a special X-ray table 1, above which an X-ray source 13 is arranged, preferably in adjustable fashion. The plate 4 of the table 1 is inserted flush on the top, on two lateral longitudinal supports 3, which are preferably constructed as aluminum profiles. Beneath the table plate 4, a carriage 5 is guided on the longitudinal supports 3 such that the carriage 5 can be moved in the longitudinal direction of the table. The particular guidance arrangement 23 is indicated only schematically in FIG. 4 but can, e.g., be fashioned as a roller guide. The carriage 5 is displaced along the longitudinal supports 3 by means of a positioning motor, the operation of which is described in more detail below. Since the present invention is concerned more with the configuration of the X-ray system than the mechanical details of the drive systems, any suitable drives may be employed. Accordingly, the drive systems are illustrated only schematically in the figures (see below).

The carriage 5 supports the detector (image intensifier) 6. In the case of the carriage 5 in FIG. 3, the carriage corresponds virtually to the width of the table. Alternatively, the detector 6' can be constructed with a smaller area than that of the carriage 5', in which case the detector 6' can be mounted so as to be movable transversely in a recess 7 in the carriage 5'. This ability to move the detector 6' transversely is realized, e.g., by a stepping motor. As has already been described above, preferably the stepping motors are controlled to drive the carriage 5 or 5' and the detector 6, 6' into a desired position beneath the radiation source.

Actuators for achieving the desired positioning can be fashioned in a variety of ways. One important goal, however, should be to fashion the actuators and actuator control in such a manner that the radiation source and the detector are disposed in a constant, fixed relationship to one another, e.g., always exactly opposite one another. In other words, the actuation and actuation control mimics the purely mechanical connection between the radiation source and the detector of the conventional art and thereby renders such mechanical connection superfluous. By way of example, according to one embodiment, the X-ray system can be provided with a single control device and identically weighted actuators for both the radiation source 13 and the carriage 5 with radiation detector 6. The single control device then causes the radiation source 13 and the radiation detector 6 to be driven in a one-to-one relationship, such that the detector 6 always remains directly below the radiation source 13.

Figure 1:
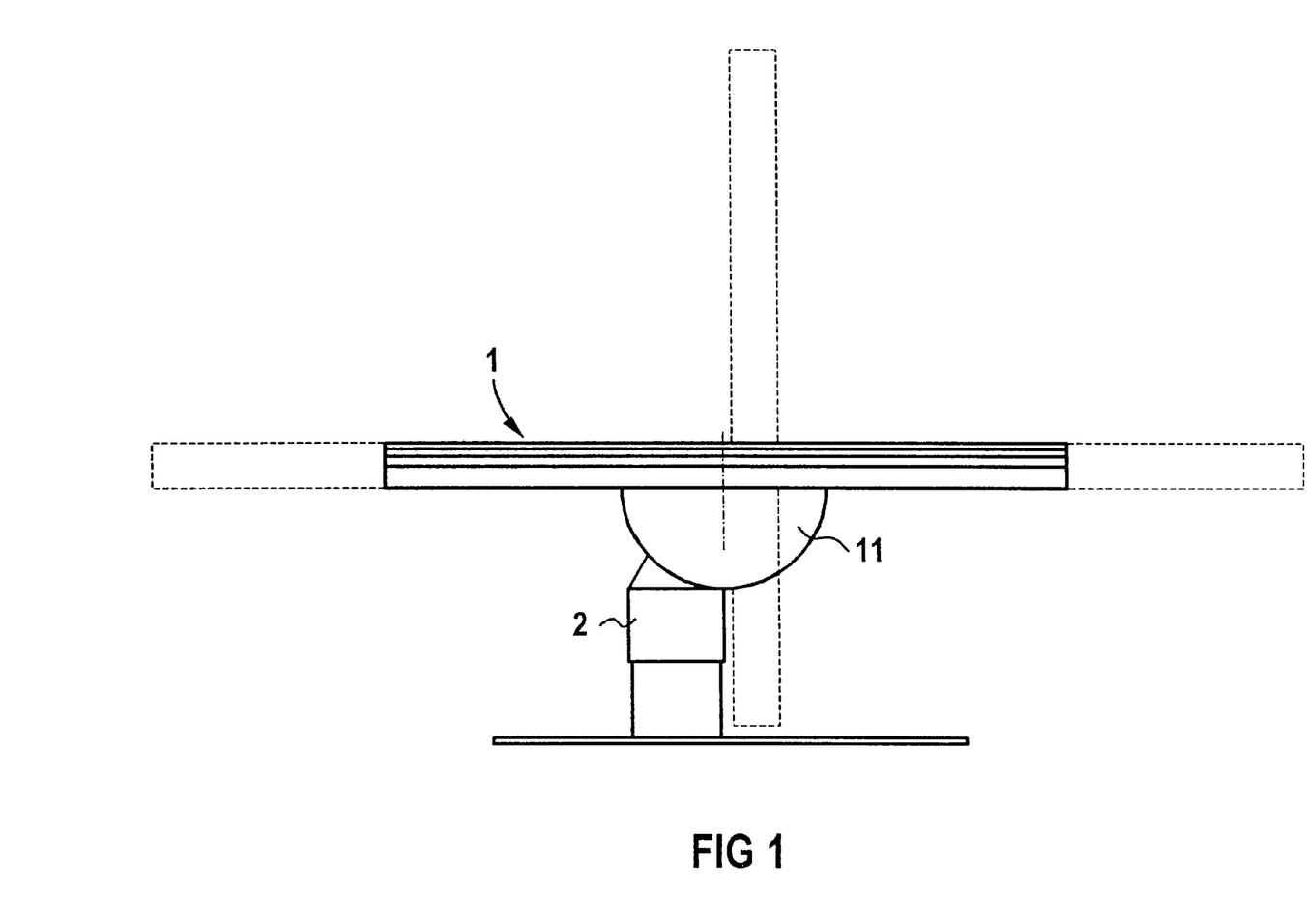
FIG. 1 shows a side view of an X-ray system according to the invention, without the radiation source to be arranged above the table.
Figure 2:
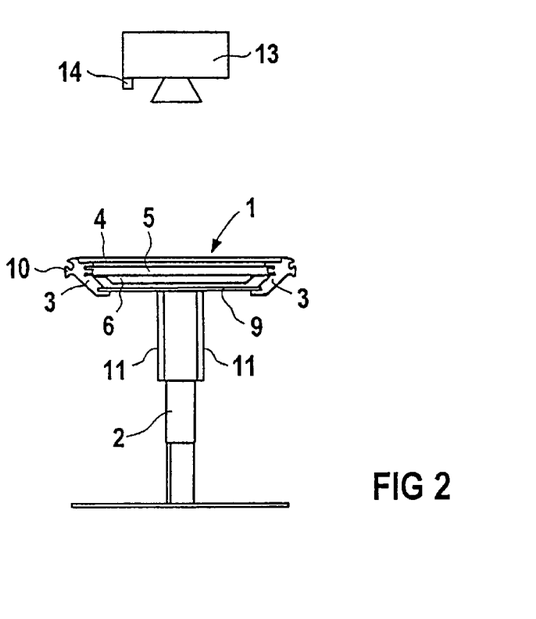
FIG. 2 shows a front view of the X-ray system according to FIG. 1, but including the radiation source.
Figure 3:
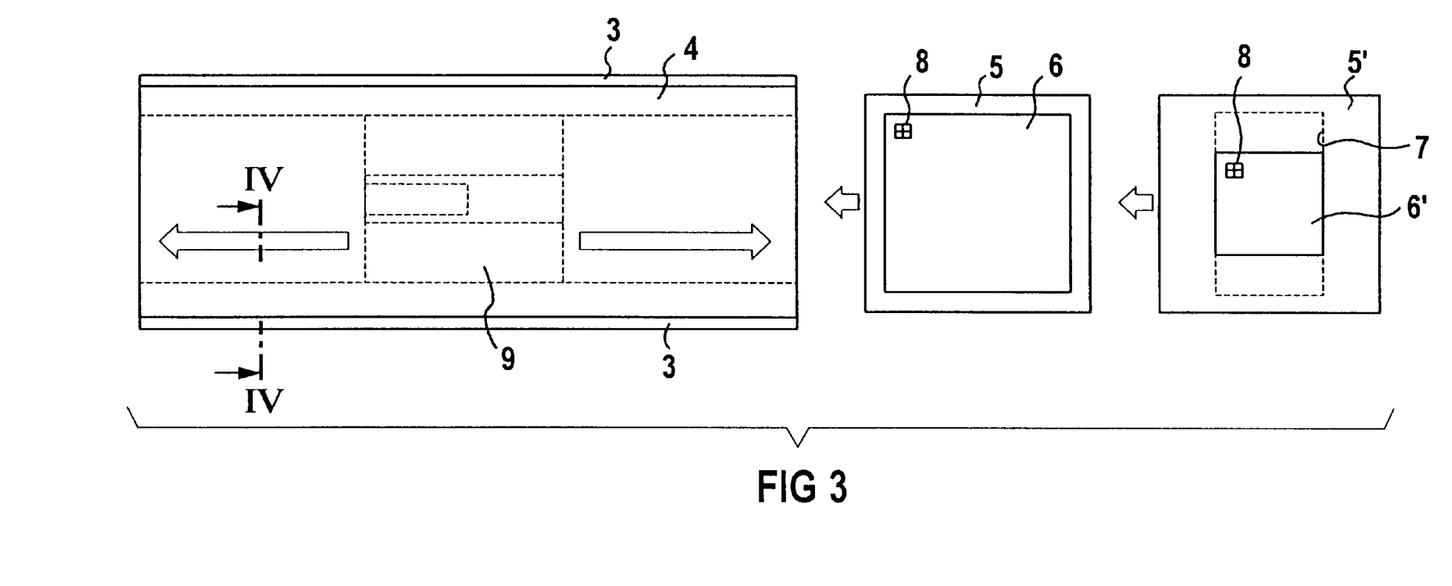
FIG. 3 shows a plan view of the table plate and two interchangeable carriages, each having a different-sized detector plate.
Figure 5:
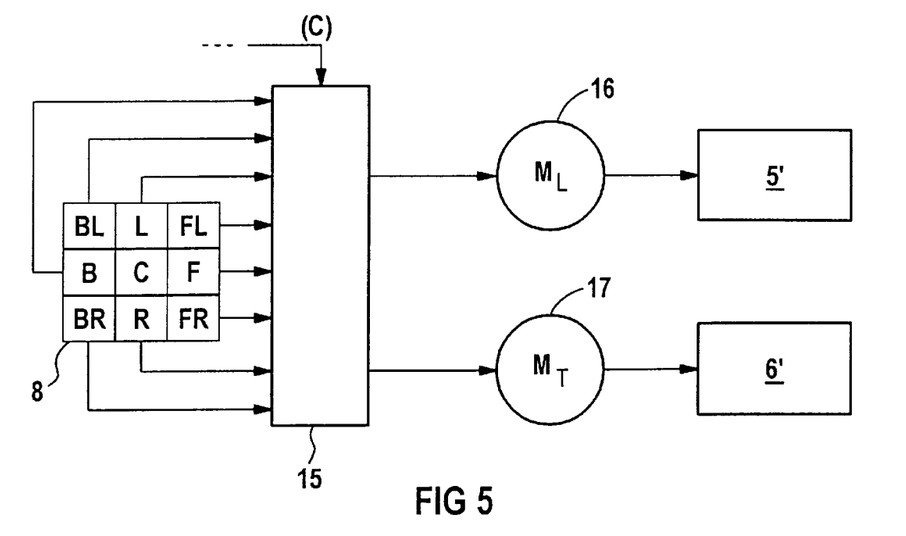
FIG. 5 illustrates, in block diagram form, an arrangement for controlling the movement of the carriage and radiation detector of the X-ray system.

According to a preferred embodiment illustrated in FIGS. 3 and 5, the detector 6 (or detector 6') is provided with a sensor or sensor section 8. The sensor 8 on the detector 6, 6' responds to a control radiation signal emitted from an emitter 14 on the radiation source 13 (see FIG. 2). Such a sensor 8 can be provided either in lieu of or in addition to the actuator control described in the previous paragraph, to achieve the desired positioning.

The sensor element 8 illustrated in FIG. 5 would be suitable for the transversely and longitudinally movable detector 6' and consists of nine subsections BL-FR, each corresponding to a different actuation direction for the detector 6'. Respective outputs from the various subsections of the sensor 8 are input into a control device 15 for processing. The control device 15, in turn, is connected to a first step motor 16 governing longitudinal motion of the detector 6' (via the carriage 5') and to a second step motor 17 governing transverse motion of the detector 6'.

In operation, each sensor subsection measures e.g. the intensity of focused radiation received from the emitter 14. Specifically, the control device 15, based on the inputs received, actuates the step motor 16 and/or the step motor 17 in an attempt to center the beam emitted by the emitter 14 on the central subsection C of the sensor 8. Accordingly, the detector 6' closely tracks every movement made by the radiation source 13, thereby maintaining its predetermined positional relationship with respect to the radiation source 13. For instance, if the detector 6' lags behind the radiation source 13, the beam emitted by the source 13 will shift from the central subsection C to the back subsection B. The control device 15 will detect this shift and compensate therefor by increasing the drive signal to the step motor 16 until the carriage 5', and thus the detector 6', is again located directly under the radiation source 13. Even though FIG. 5 shows a total of nine subsections, according to another embodiment, the corner subsections can be omitted, such that longitudinal and transverse motions are governed by five sensor subsections alone. Alternatively or additionally, the central subsection C could be omitted as well. From the disclosure given, those skilled in the art will be able to devise a variety of sensor configurations, all of which, however, should fairly fall within the scope of the present invention.

Figure 6:
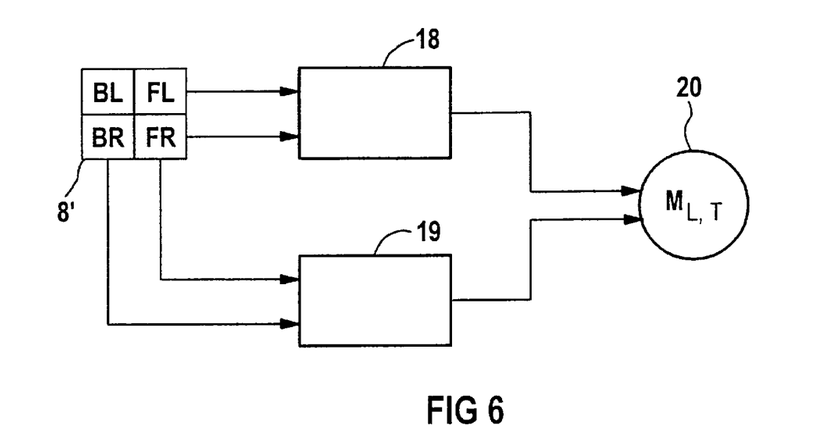
FIG. 6 illustrates, again in block diagram form, an alternative embodiment of the arrangement for controlling the movement of the carriage and radiation detector of the X-ray system

According to yet another embodiment, as illustrated in FIG. 6, the sensor 8' is divided into two sets of two subsections. Outputs from the left subsections BL and FL are input to a first comparator 18 and compared to the outputs from the right subsections BR and FR, also input to the comparator 18. By comparing the relative intensity of radiation impinging on the left subsections versus the right subsections, the comparator 18 determines whether the motor 20 needs to be actuated to drive the detector (not shown) either left or right. Comparable actuation in the forward and backward directions is achieved in analogous fashion by means of the front subsections FL, FR, the back subsections BL, BR, the comparator 19, and the motor 20.

Figure 4:
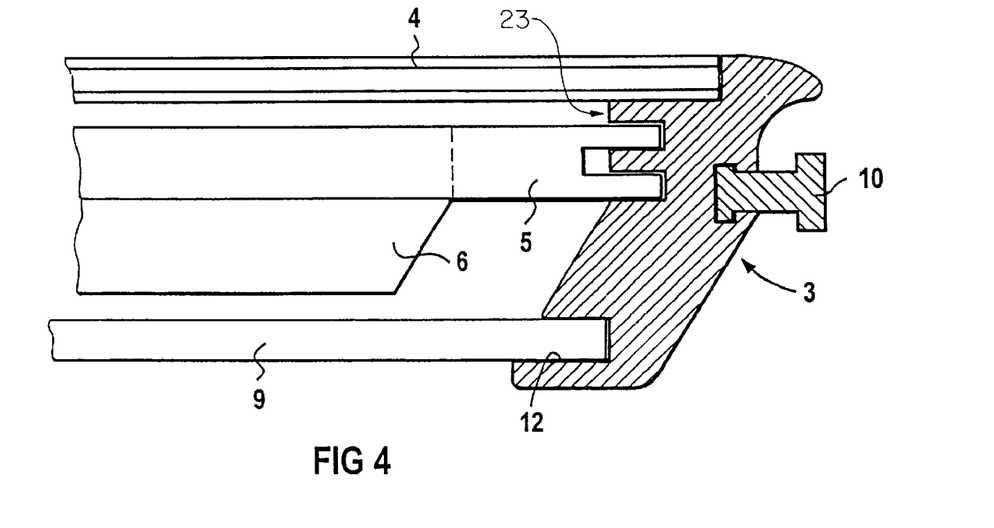
FIG. 4 shows an enlarged section along the line IV—IV in FIG. 3.

As best shown in FIG. 4, the longitudinal supports 3 are mounted on one or more cross arms 9, which are arranged beneath the detector 6. In the case where the cross arms 9 are rigidly connected to the longitudinal supports 3, the ability to displace the table plate in the longitudinal direction does not exist. However, a longitudinal displacement (indicated by dashed lines in FIG. 1) is rendered possible by allowing the bearing of the cross arms to be displaced laterally e.g. in guides 12 of the longitudinal supports 3. In this case it would also be possible to provide rolling guidance in addition to sliding guidance.

Figure 7:
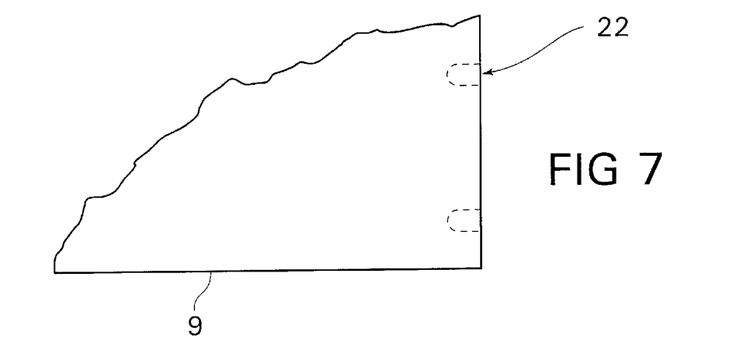
FIGS. 7–11 illustrate examples of locking and coupling mechanisms between a longitudinal support and a cross arm.
Figure 8:
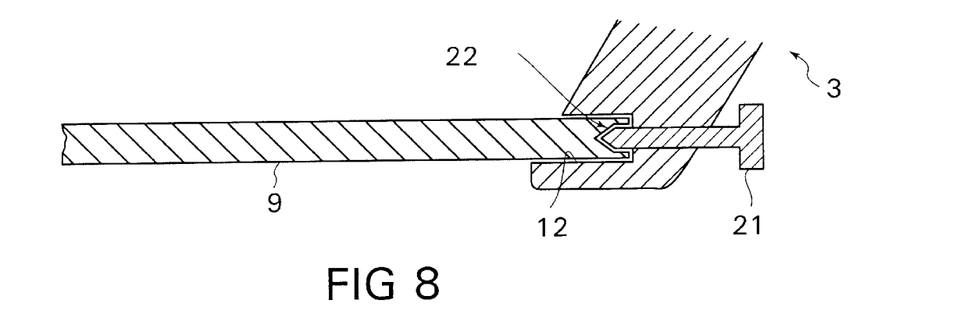
Figure 9:
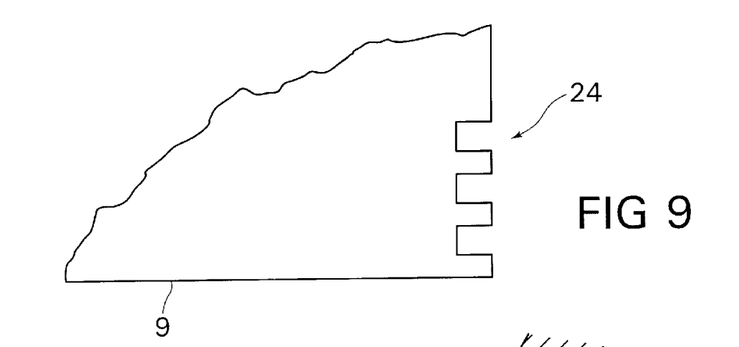
Figure 10:
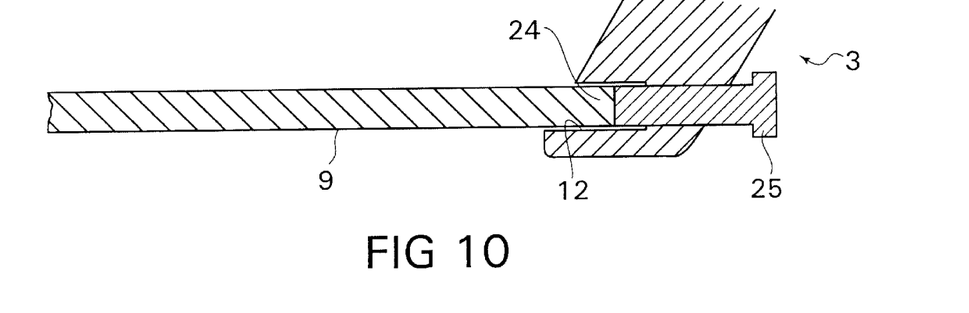
Figure 11:
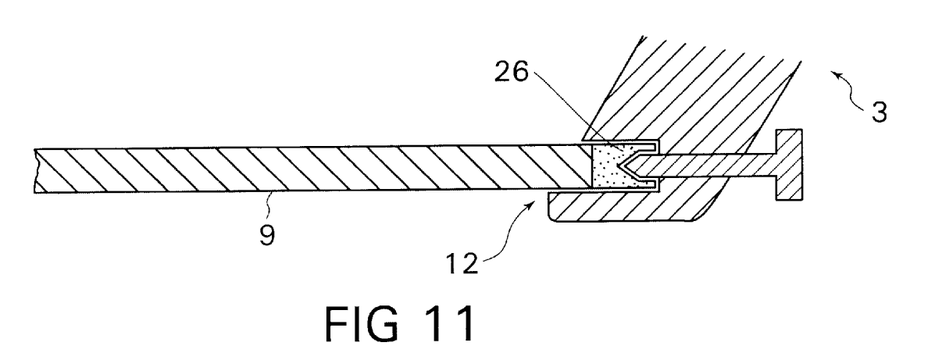

In any case, it must be possible to lock the guide of the cross arms 9 in the longitudinal supports 3. FIGS. 7–8 show one of several suitable locking mechanisms, whereby a bolt 21 retractably lodged within the longitudinal support 3 engages a corresponding locking hole 22 in the cross arm 9. The locking mechanism could equally well be fashioned as a toothed rail 24 and associated bolts 25, as shown in FIGS. 9–10 or as a brake pad 26 frictionally engaging the cross arm 9 as shown in FIG. 11.

A locking mechanism as described above is necessary, e.g., because otherwise the table would slide when it is placed in a sloping position with respect to the horizontal. The patient table is preferably provided with a maximum possible adjustment in the vertical direction of 90°, as indicated by dashes in FIG. 1. Reference numerals at 11 in FIGS. 1 and 2 indicate lateral cheeks which are fastened to the cross arm 9 and which allow the table plate 4 to be inclined with respect to the horizontal, as addressed above. A steel rail 10, which is best seen in FIG. 4, can be used to attach accessories to the table in an adjustable fashion.

The invention is not limited to the exemplary embodiments represented. A predominant feature of the invention consists in avoiding a C-arm, which is conventionally used to position the radiation source and the detector opposite one another but which has the associated drawback of blocking one side of the patient table. Instead, according to the invention, the detector is mounted such that it can be adjusted by means of positioning motors and a guided carriage beneath the table plate. The corresponding positioning of the detector is performed by means of a control device, which matches the position and alignment of the detector to that of the radiation source.

The above description of the preferred embodiments has been given by way of example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. An X-ray system comprising:
   a patient table extending in a longitudinal direction and comprising a table plate;
   a radiation detector;
   a carriage provided beneath the table plate and supporting said radiation detector under the table plate;
   lateral longitudinal supports affixed to said patient table and extending along said patient table in the longitudinal direction;
   a stand supporting said patient table; and
   at least one cross arm fastened to said stand and arranged beneath said radiation detector,
      wherein said lateral longitudinal supports comprise guides for mounting said carriage to said lateral longitudinal supports such that said carriage, along with said radiation detector, is slidably displaceable along said patient table in the longitudinal direction, and
      wherein said lateral longitudinal supports are mounted to said at least one cross arm.

2. The X-ray system as claimed in claim 1, further comprising:
   a radiation source displaceable along said patient table; and
   an actuator for driving said carriage, along with said radiation detector, along said patient table in accordance with the displacement of said radiation source along said patient table.

3. The X-ray system as claimed in claim 1, wherein said actuator comprises a step motor.

4. The X-ray system as claimed in claim 1, wherein said radiation detector comprises a cassette holder.

5. The X-ray system as claimed in claim 1, wherein said lateral longitudinal supports support and are connected to the table plate.

6. The X-ray system as claimed in claim 5, wherein said lateral longitudinal supports are permanently connected to the table plate.

7. The X-ray system as claimed in claim 1,
   wherein said lateral longitudinal supports comprise guides for receiving said at least one cross arm such that said cross arm is slidably displaceable along said patient table in the longitudinal direction at least from a first fixed position to a second fixed position.

8. The X-ray system as claimed in claim 7, further comprising:
   a plurality of locking holes extending along said patient table in the longitudinal direction and defining at least the first and second fixed positions; and
   at least one engaging protrusion for engaging at least one of said locking holes and thereby locking said cross arm in one of the fixed positions,
      wherein said locking holes are provided in one of said cross arm or said guides for receiving said at least one cross arm, and said at least one engaging protrusion is provided in the other of said cross arm or said guides for receiving said at least one cross arm.

9. The X-ray system as claimed in claim 7, further comprising:
   at least one toothed rail extending in the longitudinal direction along at least one of said guides for receiving said at least one cross arm; and
   at least one recessable bolt provided on said cross arm for engaging said at least one toothed rail and thereby locking said cross arm selectively in one of a plurality of fixed positions.

10. The X-ray system as claimed in claim 7, further comprising:
    at least one brake pad provided on at least one of said lateral longitudinal supports for releasably engaging said cross arm.

11. The X-ray system as claimed in claim 2,
    wherein said carriage is provided with a transverse recess for receiving and mounting said radiation detector such that said radiation detector is slidably displaceable in a direction transverse to the longitudinal direction; and
    further comprising a further actuator for driving said radiation detector in the transverse recess in the transverse direction.

12. The X-ray system as claimed in claim 2, further comprising:
    an actuator for driving said radiation source along said patient table; and
    a control device for outputting control signals to both said carriage actuator and to said radiation source actuator,
       wherein said control device causes said radiation source and said carriage to be driven in unison, thereby providing a fixed relative positional relationship between said radiation source and said carriage.

13. The X-ray system as claimed in claim 2, further comprising:
    an actuator for driving said radiation source along said patient table;
    a sensor provided on said radiation detector for receiving a signal output from said radiation source; and
    a control device for evaluating the signal received by said sensor and for driving said carriage actuator so as to match the displacement of said radiation source along said patient table.

14. The X-ray system as claimed in claim 12, further comprising:
    a sensor provided on said radiation detector for receiving a signal output from said radiation source,
       wherein said control device additionally evaluates the signal received by said sensor and supplies correction signals to said carriage actuator for correcting displacements of said carriage to thereby match the displacement of said radiation source along said patient table.

15. The X-ray system as claimed in claim 12, wherein said carriage actuator and said radiation source actuator both comprise step motors.

16. The X-ray system as claimed in claim 7, further comprising:

pivotable cheeks mounted between said stand and said at least one cross arm, such that said at least one cross arm and said patient table are pivotable relative to said stand at least from a first fixed position to a second fixed position.

17. The X-ray system as claimed in claim 1, further comprising at least one steel rail inserted into a slot in at least one of said lateral longitudinal supports, said steel rail being provided for adjustably attaching accessories to said patient table.

18. The X-ray system as claimed in claim 1, wherein said patient table is laterally symmetrically supported by said stand.

\* \* \* \* \*